(12) United States Patent
Itakura et al.

(10) Patent No.: US 7,387,024 B2
(45) Date of Patent: Jun. 17, 2008

(54) CAPACITIVE TYPE HUMIDITY SENSOR

(75) Inventors: Toshikazu Itakura, Toyota (JP); Hisanori Yokura, Chiryu (JP)

(73) Assignee: DENSO CORPORATION, Kariya (JP)

( * ) Notice: Subject to any disclaimer, the term of this patent is extended or adjusted under 35 U.S.C. 154(b) by 144 days.

(21) Appl. No.: 11/061,448

(22) Filed: Feb. 22, 2005

(65) Prior Publication Data
US 2005/0188764 A1 Sep. 1, 2005

(30) Foreign Application Priority Data
Feb. 27, 2004 (JP) ............................. 2004-054664

(51) Int. Cl.
*G01N 27/22* (2006.01)
*G01R 27/26* (2006.01)

(52) U.S. Cl. .................................................. 73/335.04
(58) Field of Classification Search ............. 73/335.04, 73/29.01, 29.02
See application file for complete search history.

(56) References Cited

U.S. PATENT DOCUMENTS

| | | | |
|---|---|---|---|
| 4,515,653 A * | 5/1985 | Furubayashi et al. ......... 216/67 |
| 5,296,819 A | 3/1994 | Kuroiwa et al. | |
| 5,402,075 A * | 3/1995 | Lu et al. ...................... 324/664 |
| 5,814,726 A | 9/1998 | Mitter | |
| 6,483,324 B1 | 11/2002 | Mitter et al. | |
| 6,580,600 B2 | 6/2003 | Toyoda et al. ............... 361/523 |
| 6,628,501 B2 | 9/2003 | Toyoda | |
| 6,647,782 B2 | 11/2003 | Toyoda | |
| 6,997,043 B2 * | 2/2006 | Swanson et al. .............. 73/49.3 |
| 7,112,443 B2 * | 9/2006 | Hajduk et al. ................. 436/5 |
| 2002/0136664 A1 | 9/2002 | Lee et al. | |
| 2002/0141136 A1 | 10/2002 | Toyoda et al. | |

FOREIGN PATENT DOCUMENTS

| | | |
|---|---|---|
| EP | 0 640 831 A | 3/1995 |
| JP | 51-94281 | 1/1950 |
| JP | A-7-146273 | 6/1995 |
| JP | A-08-23542 | 1/1996 |
| JP | Y2-2592782 | 1/1999 |

OTHER PUBLICATIONS

Search Report from French Patent Office issued on May 22, 2006 for the corresponding French patent application No. FR 0501900 (a copy thereof).
Search Report from French Patent Office issued on May 22, 2006 for the corresponding French patent application No. FR 0501900 (a copy thereof).
Notice of reason for refusal with English translation dated on Apr. 18, 2007 in the corresponding Japanese application No. 2004-054664.

* cited by examiner

*Primary Examiner*—Daniel S Larkin
(74) *Attorney, Agent, or Firm*—Posz Law Group, PLC (57) ABSTRACT

A capacitive type humidity sensor includes: a semiconductor substrate; a plurality of humidity devices having a capacitance variable in accordance with a humidity; a standard capacitance device having a standard capacitance, a capacitance change of which in accordance with the humidity is smaller than that of the capacitance of each humidity device; and a CV converter circuit for converting a capacitance difference between the capacitance of each humidity device and the standard capacitance of the standard capacitance device to a signal voltage. The humidity devices, the standard capacitance device and the CV converter circuit are disposed on one side of the substrate.

11 Claims, 9 Drawing Sheets

CAPACITIVE TYPE HUMIDITY SENSOR

CROSS REFERENCE TO RELATED APPLICATION

This application is based on Japanese Patent Application No. 2004-54664 filed on Feb. 27, 2004, the disclosure of which is incorporated herein by reference.

FIELD OF THE INVENTION

The present invention relates to a capacitive type humidity sensor.

BACKGROUND OF THE INVENTION

Figure 12:
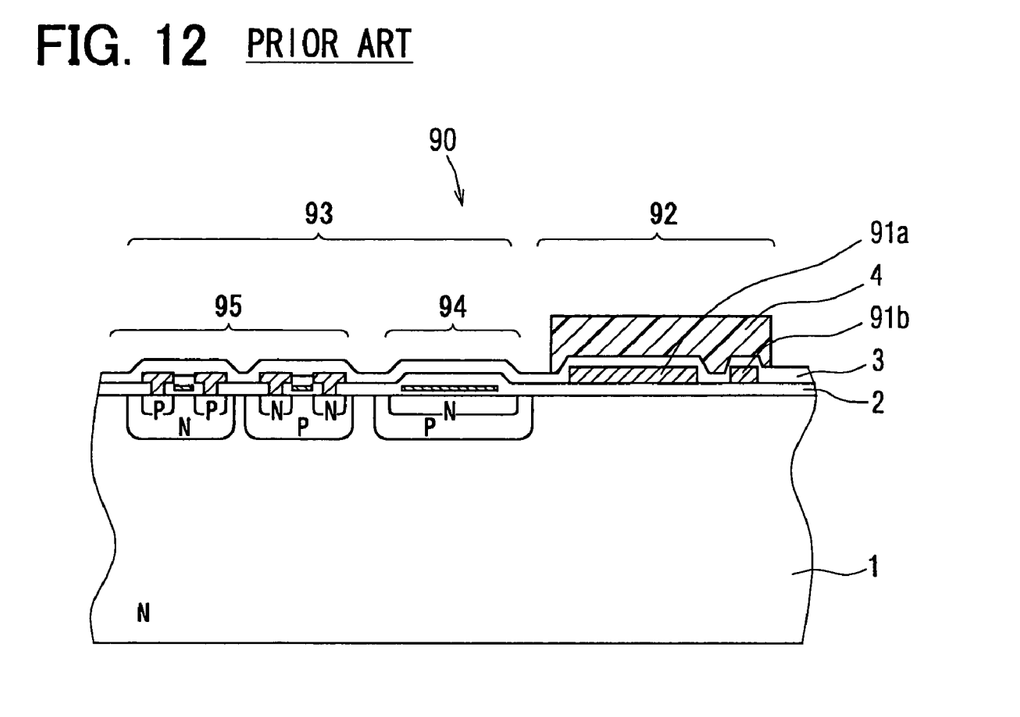
FIG. 12 is a schematic cross sectional view showing a main part of a capacitive type humidity sensor according to a prior art.

A capacitive type humidity sensor is disclosed in, for example, U.S. Pat. No. 6,580,600. The sensor includes a humidity device, a capacitance of which is variable in accordance with humidity around the device. The above sensor 90 is shown in FIG. 12. The sensor 90 includes a semiconductor substrate 1 having one surface, on which a moisture sensitive portion 92 and a circuit portion 93 are disposed.

In the moisture sensitive portion 92, a silicon oxide film 2 as an insulation film is formed on the semiconductor substrate 1. A pair of electrodes 91a, 91b is formed on the silicon oxide film 2 in such a manner that one of the electrodes 91a, 91b faces and is disposed apart from the other one of the electrodes 91a, 91b. A silicon nitride film 3 as a protection film and a moisture sensitive film 4 are formed on the substrate 1 to cover the electrodes 91a, 91b. The moisture sensitive film 4 is made of material, dielectric constant of which is variable in accordance with moisture change of atmosphere. Accordingly, the capacitance of a capacitor formed between the electrodes 91a, 91b in the moisture sensitive portion 92 is also variable in accordance with the moisture change of the atmosphere.

The circuit portion 93 includes a standard capacitance portion (i.e., a reference capacitance portion) 94 and a CMOS transistor portion 95. The capacitance change of the capacitor between the electrodes 91a, 91b in the moisture sensitive portion 92 is compared with the standard capacitance of the standard capacitance portion 94, and then, the comparison data is processed in the CMOS transistor portion 95. Thus, in the capacitive type humidity sensor 90, the capacitance change of the capacitor between the electrodes 91a, 91b in accordance with the moisture change of the atmosphere is measured so that the moisture of the atmosphere is detected.

The circuit portion 93 having the standard capacitance portion 94 and the CMOS transistor portion 95 and the moisture sensitive portion 92 are integrally formed on the substrate 1 so that the sensor 90 is integrated. Therefore, the dimensions of the sensor 90 are minimized. Further, the sensor 90 can be formed by a conventional semiconductor manufacturing method; and therefore, a manufacturing cost of the sensor 90 becomes lower.

However, when multiple humidities obtained from different sources are detected at the same time, multiple humidity sensors 90 are necessitated for detecting multiple humidities. Accordingly, the dimensions of a sensor system of the humidity sensors 90 and the weight of the sensor system are increased as the number of measurement sources becomes larger. Further, a manufacturing cost of the sensor system becomes higher.

SUMMARY OF THE INVENTION

In view of the above-described problem, it is an object of the present invention to provide a capacitive type humidity sensor capable of detecting multiple humidities at the same time. Further, the sensor has a small size and a low manufacturing cost.

A capacitive type humidity sensor includes: a semiconductor substrate; a plurality of humidity devices having a capacitance variable in accordance with a humidity; a standard capacitance device having a standard capacitance, a capacitance change of which in accordance with the humidity is smaller than that of the capacitance of each humidity device; and a CV converter circuit for converting a capacitance difference between the capacitance of each humidity device and the standard capacitance of the standard capacitance device to a signal voltage. The humidity devices, the standard capacitance device and the CV converter circuit are disposed on one side of the substrate.

The above sensor can independently detect multiple humidities of the atmospheric gases introduced from different passages at the same time. Further, the humidity devices, the standard capacitance device and the CV converter circuit are integrated in the substrate so that the dimensions of the sensor becomes smaller and the manufacturing cost of the sensor becomes lower.

Preferably, the standard capacitance of the standard capacitance device is constant without depending on the humidity.

Preferably, the humidity device is a comb-teeth electrode capacitance device having a pair of comb-teeth electrodes. The comb-teeth electrodes are disposed on the substrate to face and to engage each other. The humidity device includes a moisture sensitive film disposed on the substrate to cover the comb-teeth electrodes. The moisture sensitive film has a dielectric constant variable in accordance with the humidity. More preferably, the standard capacitance device is a comb-teeth electrode capacitance device having a pair of comb-teeth electrodes. The comb-teeth electrodes are disposed on the substrate to face and to engage each other.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

First Embodiment

A capacitive type humidity sensor according to a first embodiment of the present invention is described as follows. Firstly, an operation of the sensor is described with reference to FIGS. 1A to 1C.

Figure 1A:
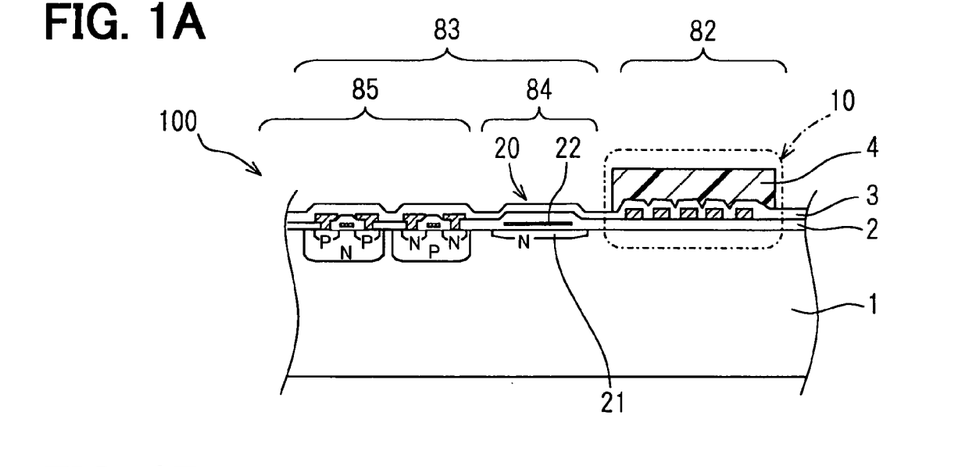
FIG. 1A is a schematic cross sectional view showing a main part of a capacitive type humidity sensor according to a first embodiment of the present invention.
Figure 1B:
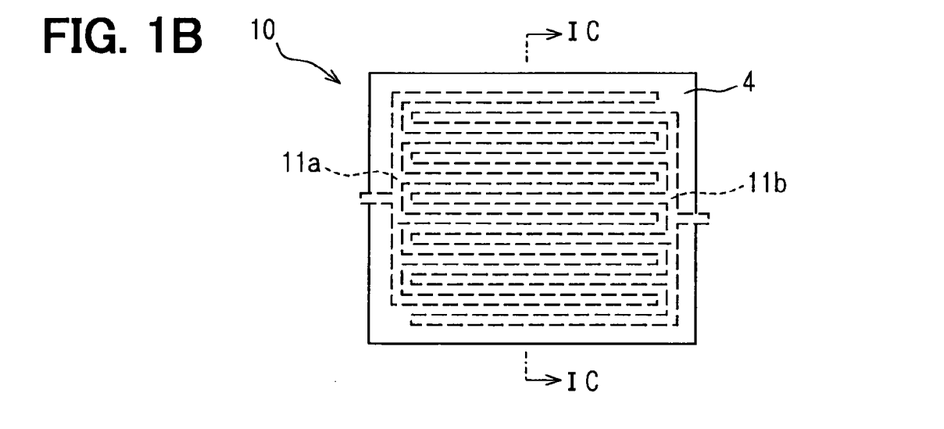
FIG. 1B is a plan view showing a humidity device of the sensor.
Figure 1C:
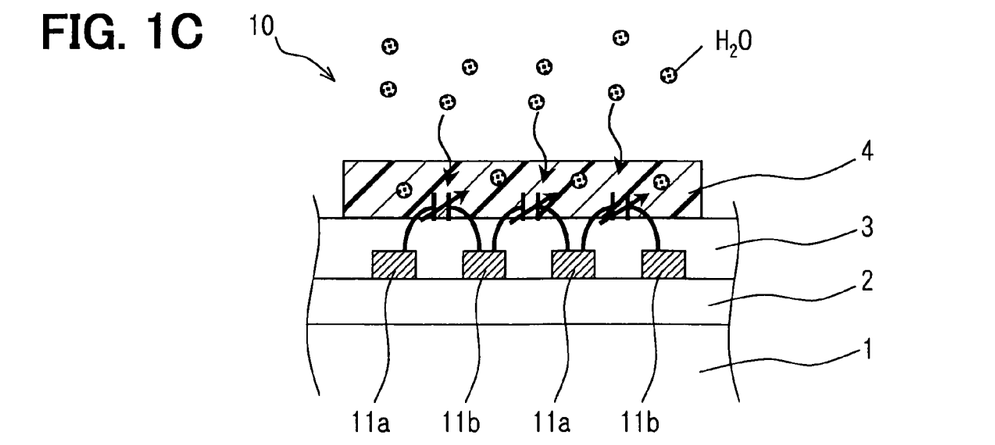
FIG. 1C is a partially enlarged cross sectional view showing the humidity device taken along line IC-IC in FIG. 1B.

FIG. 1A shows a main part 100 of the sensor 101 (illustrated in FIG. 2) schematically, and FIGS. 1B and 1C show a humidity device 10 of the main part 100.

The main part 100 of the sensor 101 includes a semiconductor substrate 1 having one surface, on which a moisture sensitive portion 82 and a circuit portion 83 are disposed. The moisture sensitive portion 82 includes the humidity device 10. The substrate 1 is made of silicon. The circuit portion 83 includes a CMOS transistor portion 85 and a standard capacitance portion 84. The standard capacitance portion 84 includes a standard capacitance device 20.

The humidity device 10 includes a pair of comb-teeth electrodes 11a, 11b, which is disposed separately on the substrate 1 to face each other. Specifically, comb-teeth of one electrode 11a engage corresponding comb-teeth of the other electrode 11b. Thus, the comb-teeth electrodes 11a, 11b provide a capacitor. The comb-teeth electrodes 11a, 11b are made of wiring material such as aluminum. The capacitance of the capacitor formed between the comb-teeth electrodes 11a, 11b is much larger than that formed between the electrodes 91a, 91b shown in FIG. 12. Thus, the humidity device 10 has a large capacitance capacitor. Further, the humidity device 10 is formed accurately and stably by a conventional semiconductor manufacturing method with low cost, compared with a humidity sensor having a pair of parallel plate electrodes. Therefore, the sensor 101 can be manufactured with low cost.

A moisture sensitive film 4 is formed on the comb-teeth electrodes 11a, 11b through a silicon nitride film 3 as a protection film to cover the comb-teeth electrodes 11a, 11b. The dielectric constant of the moisture sensitive film 4 is changed in accordance with humidity, i.e., moisture around the humidity device 10. The moisture sensitive film 4 is made of polyimide resin, and has a relative dielectric constant in a range between three and four. Here, water (i.e., $H_2O$) has a relative dielectric constant of eighty. Therefore, when the moisture sensitive film 4 absorbs or adsorbs a molecule of water, the dielectric constant of the moisture sensitive film 4 becomes larger. Therefore, the capacitance of the humidity device 10 becomes larger. Thus, the dielectric constant of the moisture sensitive film 4 is changed in accordance with the humidity change of the atmosphere around the sensor 100, and then, the capacitance of the humidity device 10 is also changed.

The standard capacitance device 20 in the main part 100 of the sensor 101 includes a parallel plate type capacitor having a pair of electrodes. One of the electrodes is provided by an N type diffusion layer 21, and the other one of the electrodes is provided by a poly silicon layer 22. The electrodes are formed in the substrate 1, and sandwich a silicon oxide film 2 as a dielectric substance. The standard capacitance device 20 does not include the moisture sensitive film 4 so that the capacitance of the device 20 does not change even when the humidity around the main part 100 of the sensor 101 is changed.

The capacitance change of the humidity device 10 in accordance with the humidity change of the atmosphere is compared with the capacitance of the standard capacitance device 20 as a reference. The comparison data is processed in the CMOS transistor portion 85. Thus, the sensor 101 detects the humidity around the sensor 101.

Figure 2A:
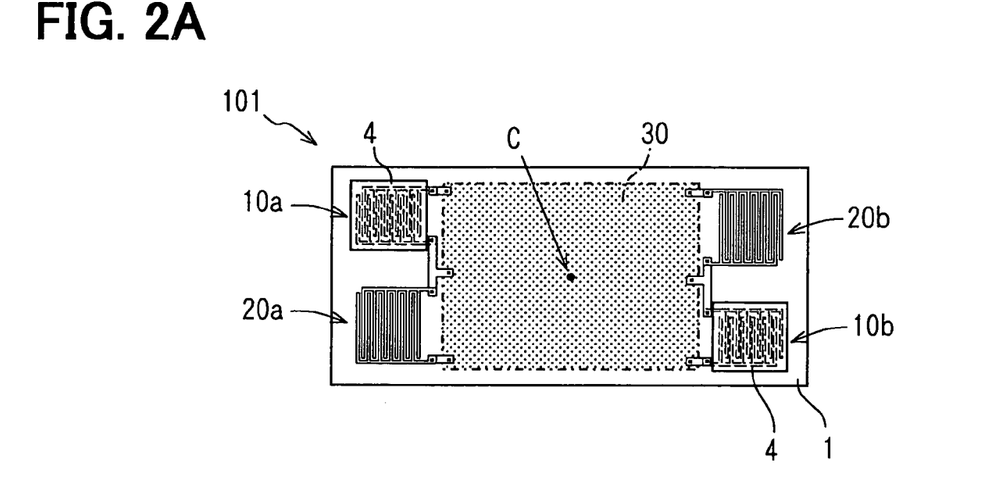
FIG. 2A is a plan view showing a capacitive type humidity sensor according to the first embodiment.
Figure 2B:
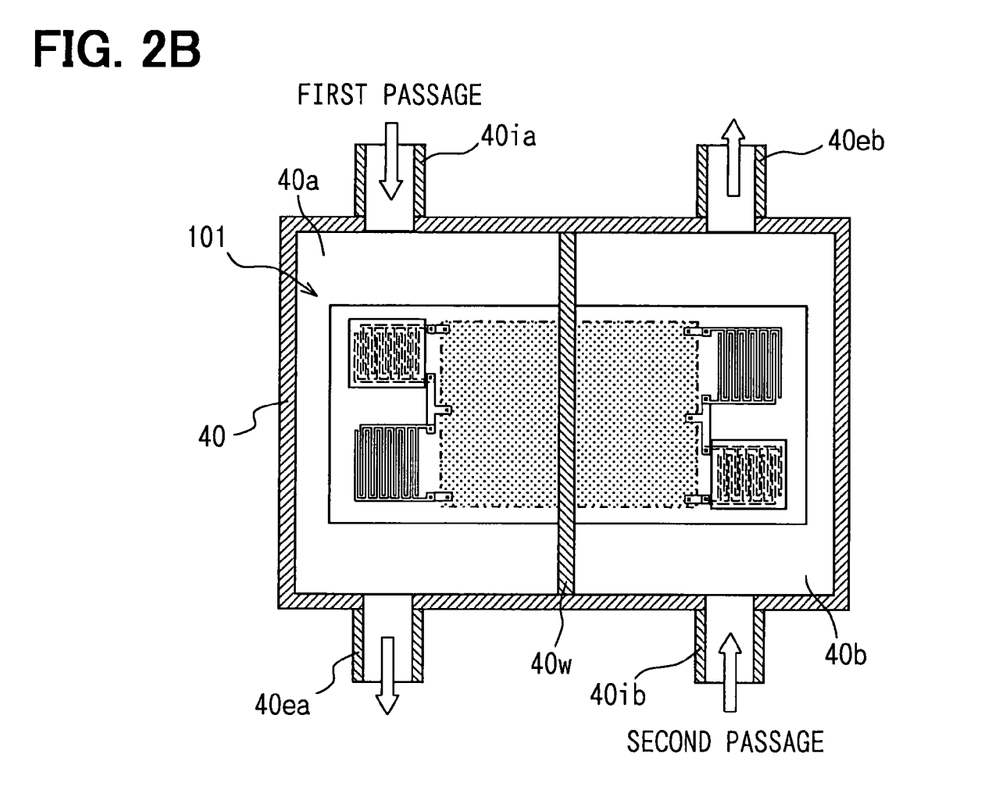
FIG. 2B is a plan view showing the sensor accommodated in a casing.

The whole construction of the sensor 101 is shown in FIG. 2A. FIG. 2B shows a detection system having the sensor 101.

The sensor 101 includes a pair of humidity devices 10a, 10b and a pair of standard capacitance devices 20a, 20b. Each humidity device 10a, 10b has a capacitance variable in accordance with the humidity. Each standard capacitance device 20a, 20b has a capacitance, which does not change even when the humidity is changed; or the capacitance change of the standard capacitance device 20a, 20b in accordance with the humidity is much smaller than that of the humidity device 10a, 10b. Accordingly, the capacitance of the standard capacitance device 20a, 20b can be changed a little in accordance with the humidity so that the capacitance change of the standard capacitance device 20a, 20b is much smaller than that of the humidity device 10a, 10b. The sensor 101 further includes a CV converter circuit 30 for converting the capacitance difference between the humidity device 10a, 10b and the standard capacitance device 20a, 20b to a voltage signal. The humidity devices 10a, 10b, the standard capacitance devices 20a, 20b and the CV converter circuit 30 are integrated on one surface of the substrate 1. Thus, the dimensions of the sensor 100 become smaller. Further, the sensor 101 can be formed with low cost.

The standard capacitance device 20a, 20b includes a comb-teeth electrode capacitor instead of a parallel plate electrode capacitor. No moisture sensitive film 4 is formed on the comb-teeth electrodes in the standard capacitance device 20a, 20b. Therefore, the capacitance of the standard capacitance device 20a, 20b is not changed substantially in accordance with the humidity of the atmosphere. Or the capacitance change of the standard capacitance device 20a, 20b in accordance with the humidity is set to be much smaller than that of the humidity device 10a, 10b. In a case where the capacitance of the standard capacitance device 20a, 20b is not changed even though the humidity around the sensor 100 is changed, the capacitance difference between the humidity device 10a, 10b and the standard capacitance device 20a, 20b becomes larger so that the sensor 100 detects the humidity more accurately.

In the sensor 101, each standard capacitance device 20a, 20b corresponds to the humidity device 10a, 10b. Accordingly, even if the capacitances of two humidity devices 10a, 10b are different, the capacitance of the corresponding standard capacitance device 20a, 20b can be optimally determined.

The CV converter circuit 30 corresponds to the CMOS transistor portion 85. The sensor 101 is accommodated in a casing 40 so that the humidity detection system having the sensor 100 is packaged. The casing 40 includes a separation wall 40w disposed on the sensor 100 so that the humidity detection system is separated into two parts 40a, 40b. One part is the first accommodation chamber 40a for accommodating the humidity device 10a, and the other part is the second accommodation chamber 40b for accommodating the humidity device 10b. The first accommodation chamber 40a has an inlet 40ia for introducing the gas into the chamber 40a and an outlet 40ea for discharging the gas out of the system so that the first accommodation chamber 40a provides the first system as the first gas passage. The second accommodation chamber 40b has an inlet 40ib for introducing the gas into the chamber 40b and an outlet 40eb for discharging the gas out of the system so that the second accommodation chamber 40b provides the second system as the second gas passage. Thus, two gases are introduced through two different systems into two chambers 40a, 40b independently. Thus, multiple humidities of the gases introduced from the inlets 40ia, 40ib are independently detected by the humidity devices 10a, 10b at the same time.

In the sensor 101, the substrate 1 has a substantially rectangular shape, and the CV converter 30 is disposed on the center of the substrate 1. Two humidity devices 10a, 10b are disposed on both sides of the substrate 1. Specifically, both sides of the humidity devices 10a, 10b are disposed in a longitudinal direction of the substrate 1. Further, the two humidity devices 10a, 10b are disposed symmetrically with respect to a center point C shown in FIG. 2A. Thus, a separation wall 40w of the casing 40 can be formed easily. Further, two standard capacitance devices 20a, 20b are also disposed symmetrically with respect to the center point C. Furthermore, two inlets 40ia, 40ib for introducing the atmospheric air into the casing 40 and two outlets 40ea, 40eb for discharging the introduced atmospheric air are also disposed symmetrically with respect to the center point C so that the air flow of the atmospheric air is stabilized. The atmospheric air is introduced into the casing 40 to detect the humidity of the atmospheric air.

When the conventional humidity sensor simultaneously detects multiple humidities of the atmospheric airs introduced from different passages by using multiple humidity devices disposed on the semiconductor substrates, it is required to prepare the multiple humidity devices having the number of the devices equal to the number of the passages of the atmospheric air. Therefore, the dimensions and the weight of the sensor become larger in proportion to the number of the passages. However, the capacitive type humidity sensor 101 shown in FIGS. 2A and 2B having multiple humidity devices 10a, 10b disposed on the same substrate 1 can simultaneously detect multiple humidities of the different atmospheric airs introduced from different passages. Therefore, the dimensions and the weight of the sensor 101 become smaller so that the dimensions of the sensor 101 are minimized. Further, since the dimensions of the sensor 101 are minimized, the manufacturing cost of the sensor 101 is reduced.

Thus, the capacitive type humidity sensor 101 detects multiple humidities simultaneously and independently. Further, the sensor has a small size and a low manufacturing cost.

Second Embodiment

Figure 3:
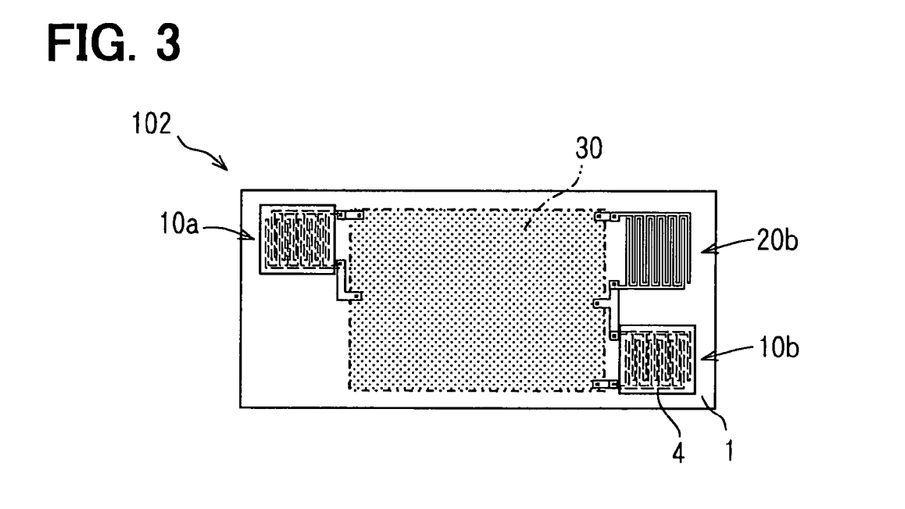
FIG. 3 is a plan view showing a capacitive type humidity sensor according to a second embodiment of the present invention.

A capacitive type humidity sensor 102 according to a second embodiment of the present invention is shown in FIG. 3. The sensor 102 includes two humidity devices 10a, 10b, one standard capacitance device 20b and the CV converter circuit 30. The humidity devices 10a, 10b share the standard capacitance device 20b commonly. Thus, in the sensor 102, the number of the standard capacitance devices 20b is reduced so that the area occupied by the standard capacitance device 20b is reduced. Thus, the dimensions of the sensor 102 are much reduced.

Third Embodiment

Figure 4A:
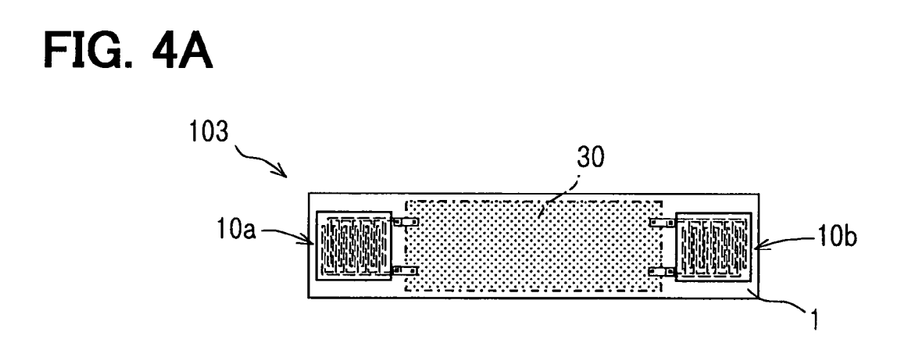
FIG. 4A is a plan view showing a capacitive type humidity sensor.
Figure 4B:
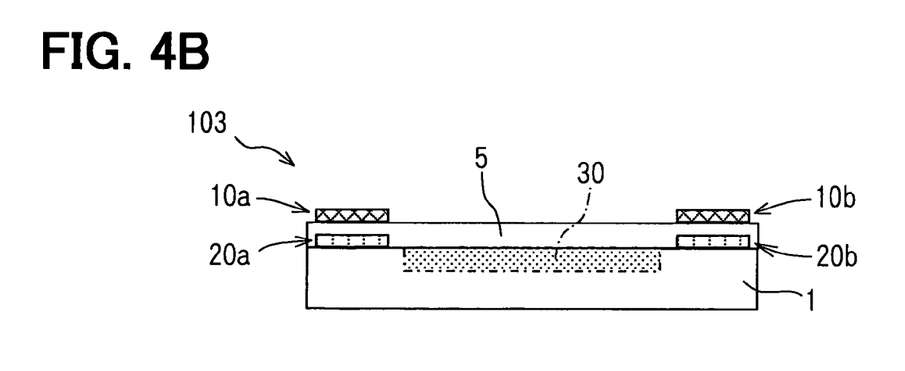
FIG. 4B is a cross sectional view showing the sensor according to a third embodiment of the present invention.

A capacitive type humidity sensor 103 according to a third embodiment of the present invention is shown in FIGS. 4A and 4B. The sensor includes two humidity devices 10a, 10b, two standard capacitance devices 20a, 20b and the CV converter circuit 30. The humidity devices 10a, 10b are disposed on the standard capacitance devices 20a, 20b through an insulation layer 5. Thus, the plan area occupied by the humidity devices 10a, 10b and the standard capacitance devices 20a, 20b is reduced since the humidity devices 10a, 10b and the standard capacitance devices 20a, 20b are laminated together. Thus, the dimensions of the sensor 103 are much reduced.

Fourth Embodiment

Figure 5A:
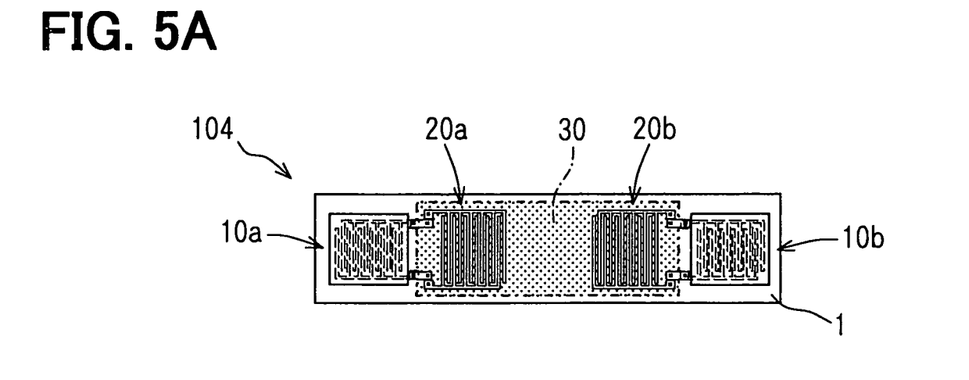
FIG. 5A is a plan view showing a capacitive type humidity sensor.
Figure 5B:
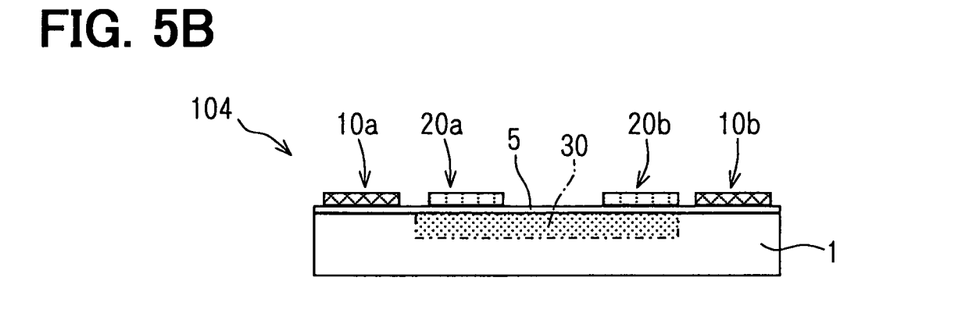
FIG. 5B is a cross sectional view showing the sensor according to a fourth embodiment of the present invention.

A capacitive type humidity sensor 104 according to a fourth embodiment of the present invention is shown in FIGS. 5A and 5B. The sensor 104 includes two humidity devices 10a, 10b, two standard capacitance devices 20a, 20b and the CV converter circuit 30. The humidity devices 10a, 10b and the standard capacitance devices 20a, 20b are disposed on the substrate 1 through the insulation layer 5. The CV converter circuit 30 is disposed under the insulation layer 5. Specifically, the humidity devices 10a, 10b and the standard capacitance devices 20a, 20b are disposed in line. The CV converter circuit 30 is disposed under the standard capacitance devices 20a, 20b.

In this case, the area occupied by the CV converter circuit 30 and the standard capacitance devices 20a, 20b is reduced. Thus, the dimensions of the sensor 104 are much reduced.

Fifth Embodiment

Figure 6:
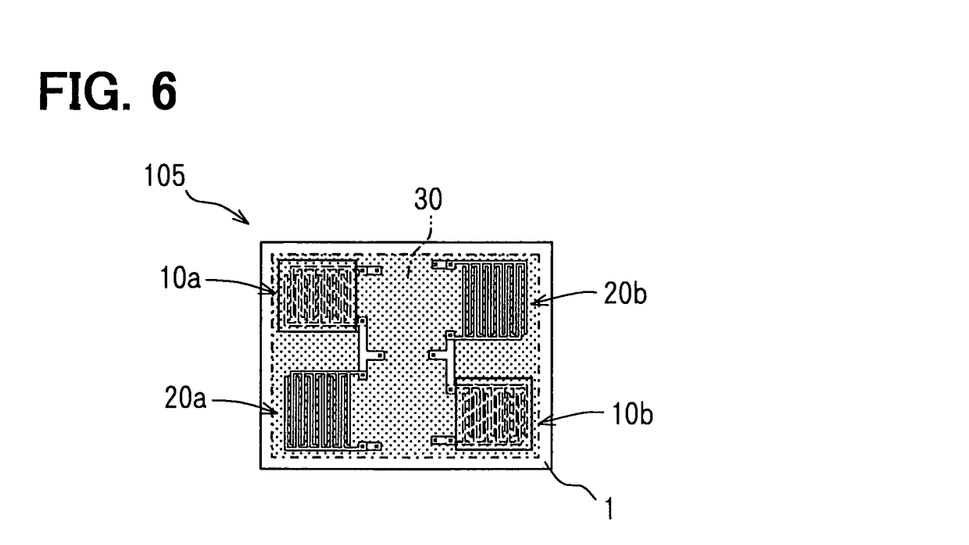
FIG. 6 is a plan view showing a capacitive type humidity sensor according to a fifth embodiment of the present invention.

A capacitive type humidity sensor 105 according to a fifth embodiment of the present invention is shown in FIG. 6. The sensor 105 includes two humidity devices 10a, 10b, two standard capacitance devices 20a, 20b and the CV converter circuit 30. The humidity devices 10a, 10b and the standard capacitance devices 20a, 20b are disposed on the substrate 1 through the insulation layer 5. The CV converter circuit 30 is disposed under the insulation layer 5. Specifically, the CV converter circuit 30 is disposed under the humidity devices 10a, 10b and the standard capacitance devices 20a, 20b.

In this case, the area occupied by the CV converter circuit 30 is reduced. Thus, the dimensions of the sensor 105 are much reduced.

Sixth Embodiment

Figure 7A:
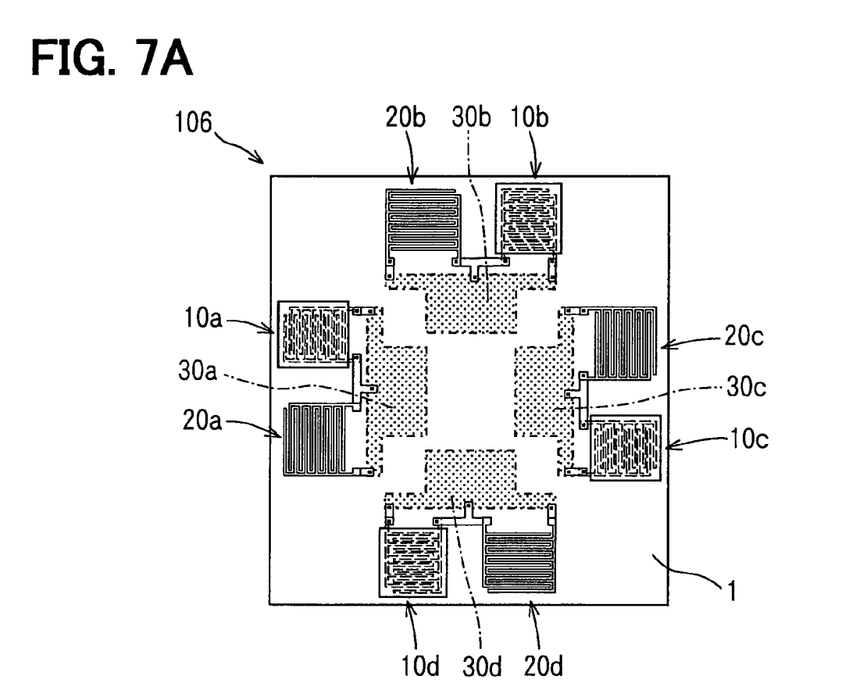
FIG. 7A is a plan view showing a capacitive type humidity sensor according to a sixth embodiment of the present invention.

A capacitive type humidity sensor 106 according to a sixth embodiment of the present invention is shown in FIG. 7A. The sensor 106 includes four humidity devices 10a-10d, four standard capacitance devices 20a-20d and four CV converter circuits 30a-30d. Each humidity device 10a-10d corresponds to the CV converter circuit 30a-30d, respectively. Since the sensor 106 includes four CV converter circuits 30a-30d corresponding to four humidity devices 10a-10d, four signals of the humidity devices 10a-10d can be processed continuously and simultaneously.

Seventh Embodiment

Figure 7B:
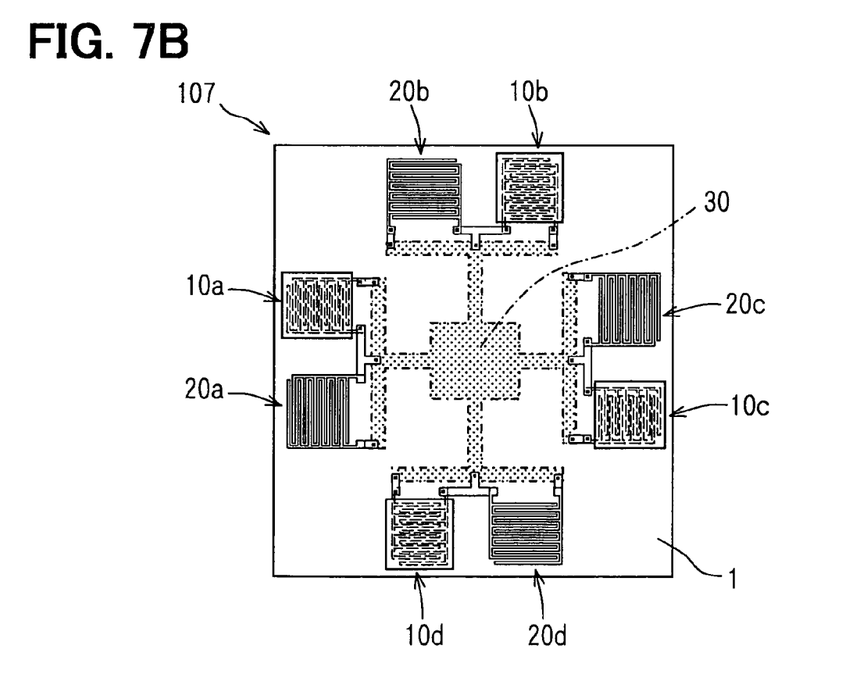
FIG. 7B is a plan view showing a capacitive type humidity sensor according to a seventh embodiment of the present invention.

A capacitive type humidity sensor 107 according to a seventh embodiment of the present invention is shown in FIG. 7B. The sensor 107 includes four humidity devices 10a-10d, four standard capacitance devices 20a-20d and the CV converter circuit 30. Four humidity devices 10a-10d share the CV converter circuit 30 commonly. The CV converter circuit 30 processes four signals of the humidity devices 10a-10d by a time-sharing mode.

In the above case, the area occupied by the CV converter circuit 30 is reduced. Thus, the dimensions of the sensor 107 are reduced.

Eighth Embodiment

Figure 8A:
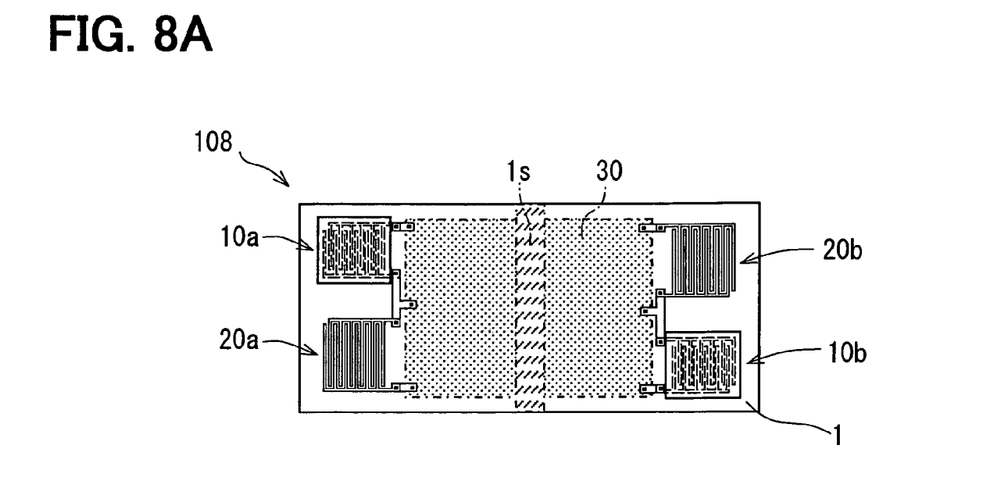
FIG. 8A is a plan view showing a capacitive type humidity sensor according to an eighth embodiment of the present invention.
Figure 8B:
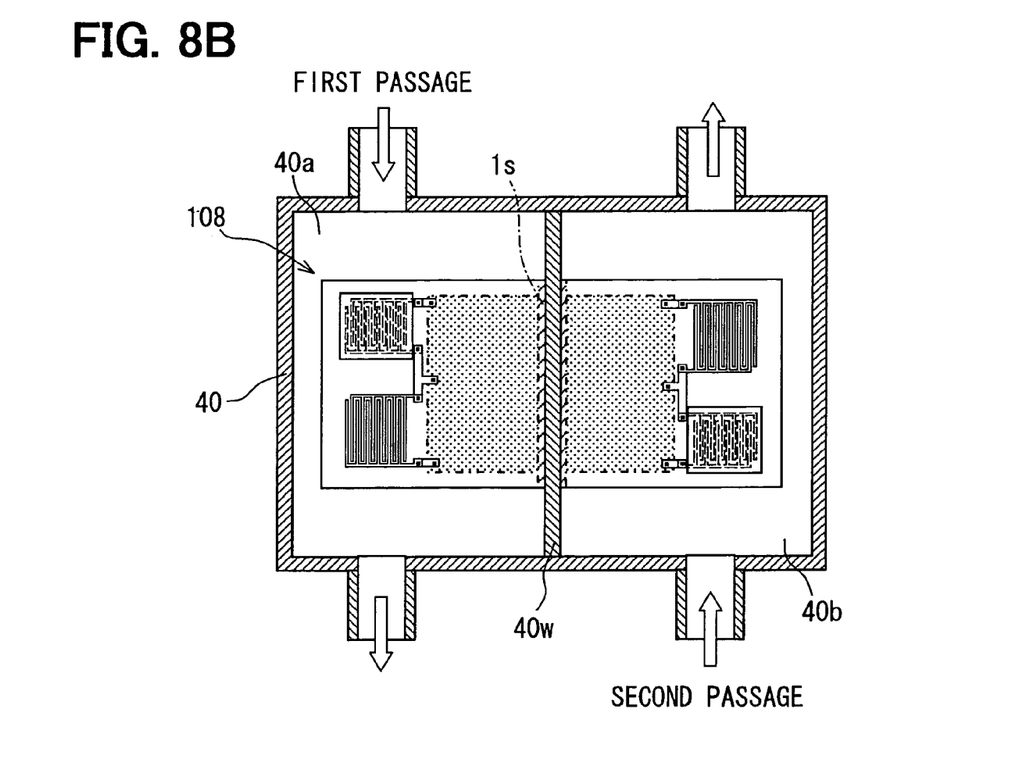
FIG. 8B is a plan view showing the sensor accommodated in a casing.

A capacitive type humidity sensor 108 according to an eighth embodiment of the present invention is shown in FIG. 8A. FIG. 8B shows the sensor 108 packaged with the casing 40.

The sensor 108 includes two humidity devices 10a, 10b, two standard capacitance devices 20a, 20b and the CV converter circuit 30. Further, the sensor 108 includes a separation region 1s for separating the CV converter circuit 30 and the humidity devices 10a, 10b. The separation region 1s in the substrate 1 has no electric circuit except for a wiring. The separation wall 40w is disposed on the separation region 1s. Thus, when the sensor 108 is packaged into the casing 40, the separation wall 40w does not break the electric circuit in the substrate 1. Further, the casing 40, i.e., the separation wall 40w can tightly contact the substrate 1, i.e., the separation region 1s so that air-tightness between the first and second accommodation chambers 40a, 40b is improved. Therefore, two atmospheric airs introduced from different inlets 40ia, 40ib are not mixed each other. Thus, the humidity in the introduced atmospheric air can be detected accurately.

Ninth Embodiment

Figure 9:
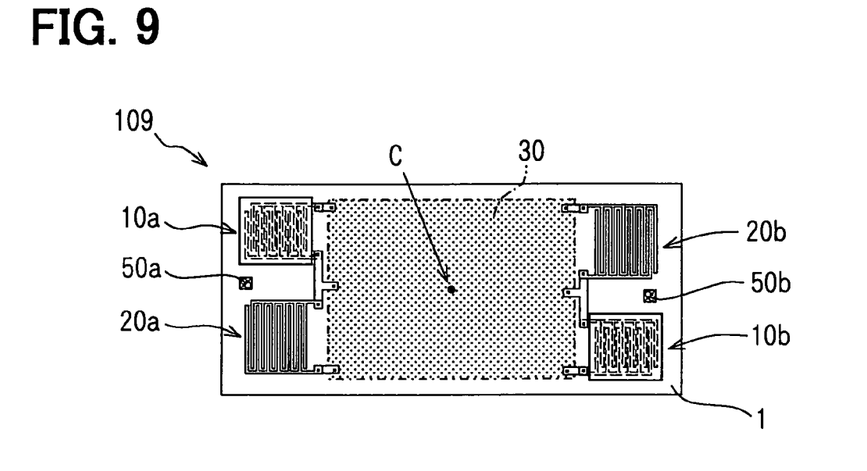
FIG. 9 is a plan view showing a capacitive type humidity sensor according to a ninth embodiment of the present invention.

A capacitive type humidity sensor 109 according to a ninth embodiment of the present invention is shown in FIG. 9. The sensor 109 includes two humidity devices 10a, 10b, two standard capacitance devices 20a, 20b and the CV converter circuit 30. Further, the sensor 109 includes two temperature sensor devices 50a, 50b, which correspond to the humidity devices 10a, 10b, respectively. The temperature sensor devices 50a, 50b are disposed symmetrically with respect to the center point C. In a case where the CV converter circuit 30 includes a heat radiation device, the temperature sensor devices 50a, 50b detect the temperature of the substrate 1 so that the heat effect derived from the heat radiation device is compensated. Specifically, the heat effect affecting to the right side humidity device 10a can be equalized to that affecting to the left side humidity device 10b. Further, a parasitic capacitance and a resistance of a wiring disposed on one side is also equalized to that of another wiring disposed on the other side. Thus, noise affecting the sensor 109 is reduced, and the influence of a power source fluctuation affecting the sensor 109 is reduced.

Tenth Embodiment

Figure 10A:
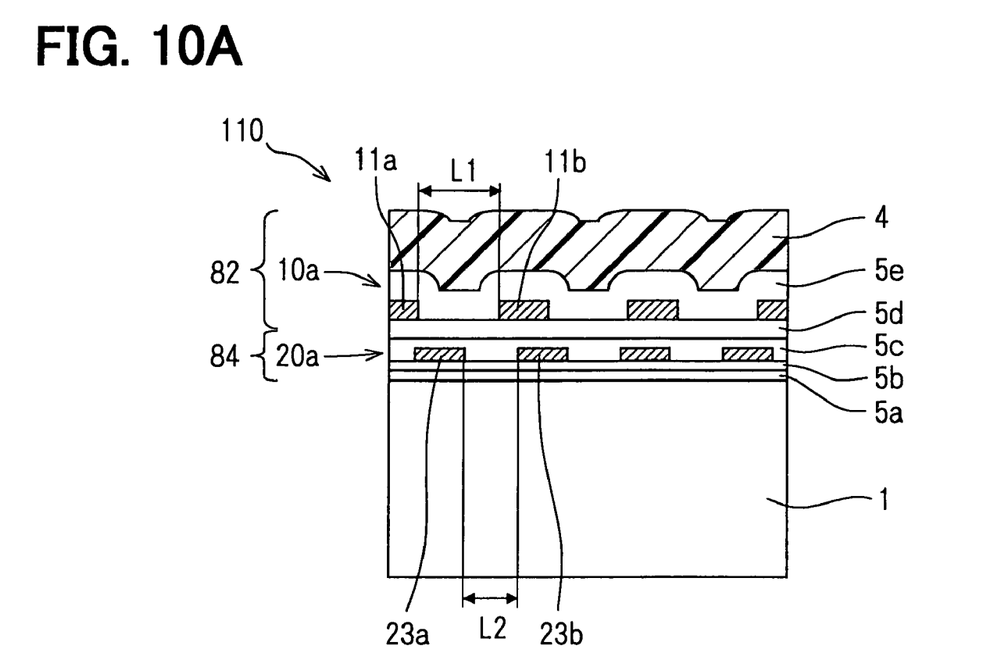
FIG. 10A is a schematic cross sectional view showing a main part of a capacitive type humidity sensor according to a tenth embodiment of the present invention.

A capacitive type humidity sensor 110 according to a tenth embodiment of the present invention is shown in FIG. 10A. The humidity device 10a is disposed on the standard capacitance device 20a through multiple insulation layers 5a-5e. Thus, the plan area occupied by the humidity device 11a and the standard capacitance device 20a is reduced since the humidity device 10a and the standard capacitance device 20a are laminated together. Thus, the dimensions of the sensor 110 are much reduced.

Here, the humidity device 10a includes a pair of comb-teeth electrodes 11a, 11b, which is disposed separately on the substrate 1 to face each other. Specifically, comb-teeth of one electrode 11a engage corresponding comb-teeth of the other electrode 11b. Thus, the comb-teeth electrodes 11a, 11b provides a capacitor. The standard capacitance device 20a includes a pair of comb-teeth electrodes 23a, 23b, which is disposed separately on the substrate 1 to face each other. Specifically, comb-teeth of one electrode 23a engage corresponding comb-teeth of the other electrode 23b. Thus, the comb-teeth electrodes 23a, 23b provide a capacitor.

The distance between the comb-teeth electrodes 11a, 11b of the humidity device 10a is defined as L1. The distance between the comb-teeth electrodes 23a, 23b of the standard capacitance device 20a is defined as L2. The distance L2 of the standard capacitance device 20a is narrower than the distance L1 of the humidity device 10a.

It is preferred that the capacitance of the humidity device 10a is equal to the standard capacitance of the standard capacitance device 20a for detecting the humidity accurately. In general, the capacitance of the humidity device 10a becomes larger since the humidity device 10a includes the moisture sensitive film 4. In the sensor 110, the distance L2 is optimized to be narrower than the distance L1 so that the standard capacitance of the standard capacitance device 20a is equalized or optimized to the capacitance of the humidity device 10a without increasing the area occupied by the standard capacitance device 20a. Thus, the sensor 110 detects the humidity more accurately.

Eleventh Embodiment

Figure 10B:
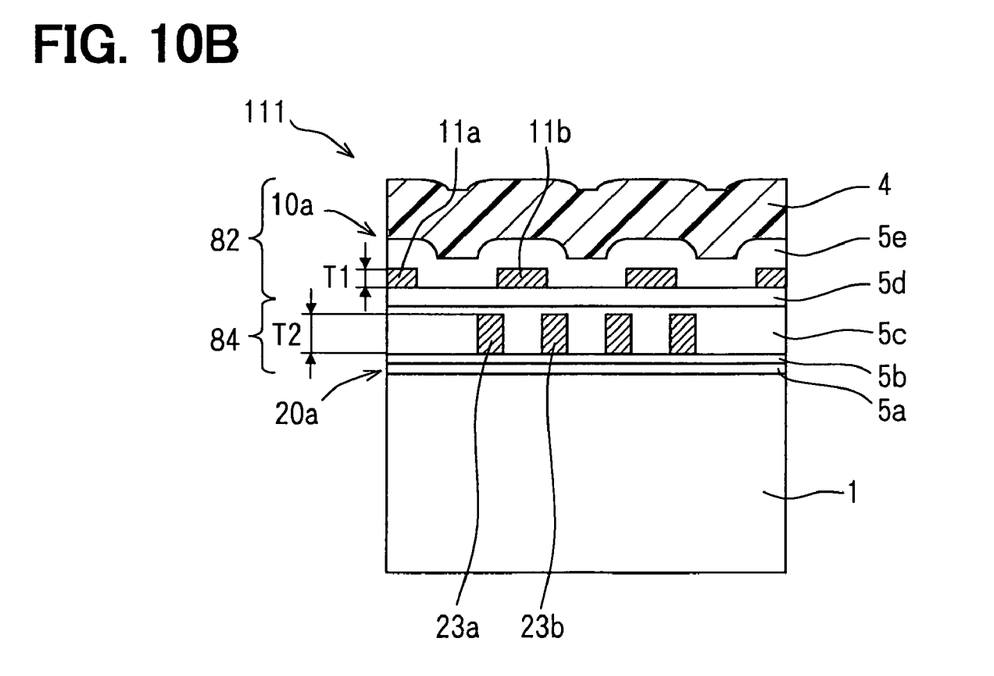
FIG. 10B is a schematic cross sectional view showing a main part of a capacitive type humidity sensor according to an eleventh embodiment of the present invention.

A capacitive type humidity sensor ill according to an eleventh embodiment of the present invention is shown in FIG. 10B. The humidity device 10a is disposed on the standard capacitance device 20a through multiple insulation layers 5a-5e. Thus, the humidity device 10a and the standard capacitance device 20a are laminated together. Accordingly, the dimensions of the sensor 110 are much reduced.

Here, the humidity device 10a includes a pair of comb-teeth electrodes 11a, 11b, which is disposed separately on the substrate 1 to face each other. The standard capacitance device 20a includes a pair of comb-teeth electrodes 23a, 23b, which is disposed separately on the substrate 1 to face each other. The height of the comb-teeth electrodes 11a, 11b of the humidity device 10a is defined as T1. The height of the comb-teeth electrodes 23a, 23b of the standard capacitance device 20a is defined as T2. The height T2 of the comb-teeth electrodes of the standard capacitance device 20a is higher than the height T1 of the comb-teeth electrodes of the humidity device 10a.

In the sensor 111, the height T2 is optimized to be higher than the height T1 so that the standard capacitance of the standard capacitance device 20a is equalized or optimized to the capacitance of the humidity device 10a without increasing the area occupied by the standard capacitance device 20a. Thus, the sensor 111 detects the humidity more accurately.

Twelfth Embodiment

Figure 11A:
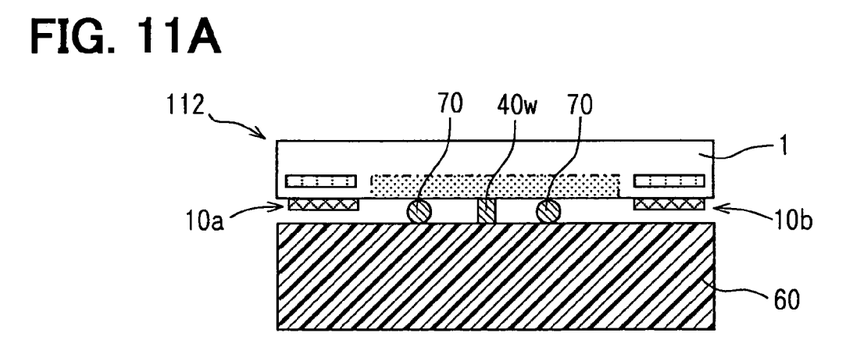
FIGS. 11A and 11B are cross sectional views showing a capacitive type humidity sensor mounted on a circuit board, according to a twelfth embodiment of the present invention.
Figure 11B:
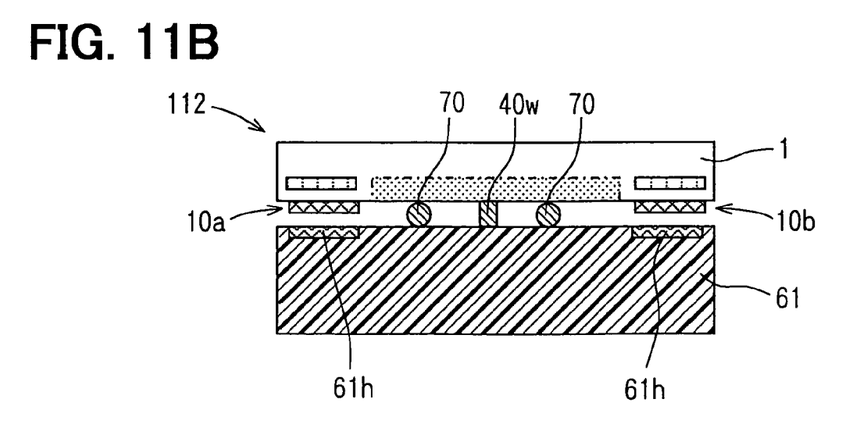

A capacitive type humidity sensor 112 according to a twelfth embodiment of the present invention is shown in FIGS. 11A and 11B. The sensor 112 is mounted on different circuit boards 60, 61. The sensor 112 includes the humidity devices 10a, 10b disposed on the standard capacitance devices 20a, 20b through the insulation layer 5. Thus, the humidity devices 10a, 10b and the standard capacitance devices 20a, 20b are laminated together. Accordingly, the dimensions of the sensor 112 are much reduced. The sensor 112 is mounted on the circuit boards 60, 61 in such a manner that one side of the sensor 112, on which the humidity devices 10a, 10b are disposed, faces the circuit boards 60, 61. Thus, the sensor 112 mounted on the circuit boards 60, 61 forms a flip chip. Specifically, the sensor 112 is bonded to the circuit boards 60, 61 through solder balls 70. In the flip chip, the clearance between the circuit boards 60, 61 and the sensor 112 becomes narrower; and therefore, no dust or no dirt is deposited on the humidity devices 10a, 10b.

The circuit board 61 further includes a heater 61h. The heater 61h is disposed on one side of the circuit board 61, which faces the sensor 112. Specifically, the heater 61h faces the humidity devices 10a, 10b. The heater 61h generates heat for removing a water drop on the humidity devices 10a, 10b. Thus, the detection accuracy of the sensor 112 is improved.

Such changes and modifications are to be understood as being within the scope of the present invention as defined by the appended claims.

What is claimed is:

1. A capacitive type humidity sensor comprising:
a semiconductor substrate;
a plurality of humidity devices having a capacitance variable in accordance with a humidity;
a plurality of standard capacitance devices having a standard capacitance, a capacitance change of which in accordance with the humidity is smaller than that of the capacitance of each humidity device;
a CV converter circuit for converting a capacitance difference between the capacitance of each humidity device and the standard capacitance of a corresponding one of the plurality of standard capacitance devices to a signal voltage; and
a casing configured to receive the semiconductor substrate, the plurality of humidity devices, the plurality of standard capacitance devices, and the CV control circuit, wherein the plurality of humidity devices, the plurality of standard capacitance devices and the CV converter circuit are disposed on one side of the substrate in a direction perpendicular to a plane of the substrate;

the casing includes at least one separation wall, which is placed on the one side of the substrate to partition an interior of the casing into a plurality of chambers;

each humidity device and the corresponding one of the plurality of standard capacitance devices are received in a corresponding one of the plurality of chambers; and the plurality of humidity devices and the plurality of standard capacitance devices are configured to be operated to simultaneously measure the humidity of gas introduced into each of the plurality of chambers.

2. The sensor according to claim 1, wherein
the standard capacitance of each of the standard capacitance devices is constant without depending on the humidity.

3. The sensor according to claim 1, wherein
the humidity devices share the CV converter circuit commonly.

4. The sensor according to claim 1, wherein
the substrate includes a separation region for separating the humidity devices, and
the separation region of the substrate has no electric part except for a wiring thereon.

5. The sensor according to claim 1, wherein
the humidity devices are disposed on the substrate to sandwich the CV converter circuit.

6. The sensor according to claim 1, wherein
the CV converter circuit is disposed on a center of the substrate, and
the humidity devices are disposed on the substrate symmetrically with respect to a center of the substrate.

7. The sensor according to claim 1, wherein
the plurality of humidity devices includes two humidity devices, and
the substrate has a rectangular shape, wherein the
the two humidity devices are disposed at two ends, respectively, of the substrate, where the two ends are opposite to each other in a longitudinal direction of the substrate.

8. The sensor according to claim 1, wherein
the humidity devices are comb-teeth electrode capacitance devices each having a pair of comb-teeth electrodes,
the comb-teeth electrodes are disposed on the substrate to face and to engage each other,
the humidity devices each include a moisture sensitive film disposed on the substrate to cover the comb-teeth electrodes, and
the moisture sensitive films have a dielectric constant variable in accordance with the humidity.

9. The sensor according to claim 8, wherein
each of the standard capacitance devices is a comb-teeth electrode capacitance device having a pair of comb-teeth electrodes, and
the comb-teeth electrodes are disposed on the substrate to face and to engage each other.

10. The sensor according to claim 9, wherein
each of the standard capacitance devices has a distance between the comb-teeth electrodes, each of the humidity devices has a distance between the comb-teeth electrodes, and the distance of each of the standard capacitance devices is narrower than that of a corresponding one of the plurality of humidity devices.

11. The sensor according to claim 9, wherein the comb-teeth electrode of each of the standard capacitance devices has a height in a vertical direction perpendicular to the substrate, the comb-teeth electrode of each of the humidity devices has a height in the vertical direction perpendicular to the substrate, and the height of the comb-teeth electrode of the standard capacitance device is higher than that of the humidity device.

* * * * *